United States Patent [19]

Runckel

[11] 4,264,987
[45] May 5, 1981

[54] GOGGLES

[76] Inventor: John L. Runckel, P.O. Box 87, Portland, Oreg. 97201

[21] Appl. No.: 62,818

[22] Filed: Aug. 1, 1979

Related U.S. Application Data

[63] Continuation-in-part of Ser. No. 957,009, Nov. 2, 1978, abandoned.

[51] Int. Cl.³ .............................................. A61F 9/02
[52] U.S. Cl. ......................................... 2/428; 2/445; 2/452; 351/128
[58] Field of Search ................... 2/428, 429, 430, 440, 2/445, 446, 452, 15; 351/128, 43

[56] References Cited

U.S. PATENT DOCUMENTS

| | | | |
|---|---|---|---|
| 1,553,010 | 9/1925 | Terry et al. | 2/15 |
| 1,964,811 | 7/1934 | Cozzens | 2/440 |
| 2,406,608 | 8/1946 | Joyce | 2/440 |
| 4,051,557 | 10/1977 | Bengtson et al. | 2/430 |
| 4,112,521 | 9/1978 | Uke | 2/452 |

FOREIGN PATENT DOCUMENTS

| | | | |
|---|---|---|---|
| 79504 | 7/1894 | Fed. Rep. of Germany | 351/128 |
| 1149068 | 7/1957 | France | 2/428 |

Primary Examiner—Peter P. Nerbun
Attorney, Agent, or Firm—Harvey B. Jacobson

[57] ABSTRACT

The goggles have two eyepieces connected by an elastomeric strap forming a nosepiece, the length of which is adjustable by loosening a pair of adjustment screws. Each eyepiece has an upper contour portion having a smooth incurve to conform to the upper eye socket. The lower portion of each eyepiece has a smooth incurve with an excurvation in the vicinity of the nosepiece to conform to the lower eye socket. Each eyepiece flares outwardly to form a widened eye socket contacting surface. Each of these surfaces slopes radially outward of the eyepiece and toward the front thereof. In this manner, when worn, the surfaces produce a radially outward pressure on the eye socket and require only a minimum layer of form padding to insure a watertight seal. The goggles are also equipped with an elastic head strap attached to a plastic hook end which fits into an aperture on one of the eyepieces for easy attachment thereto.

11 Claims, 15 Drawing Figures

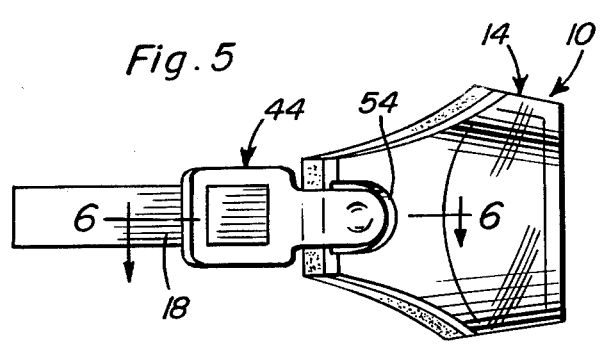
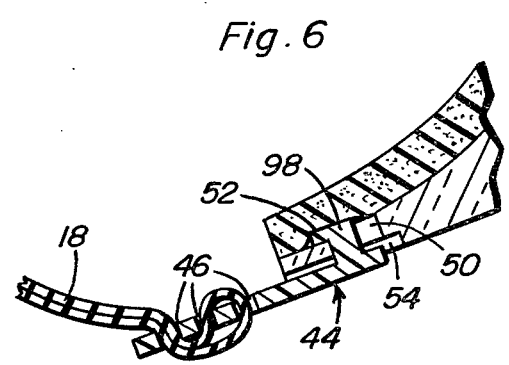
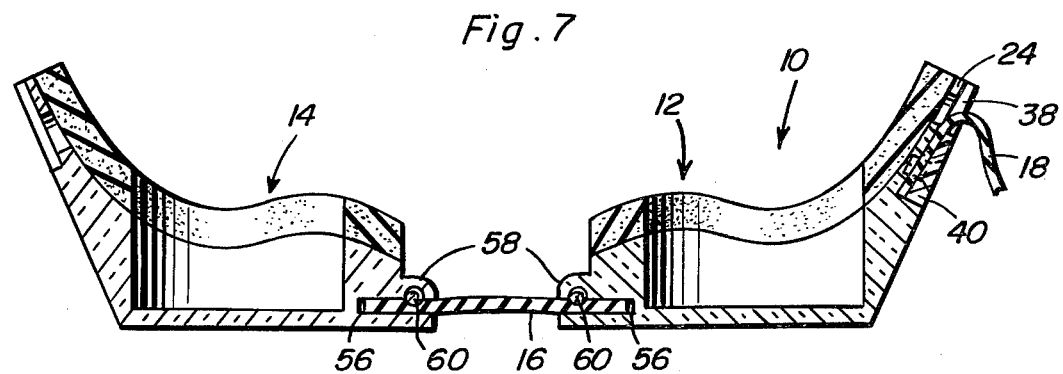
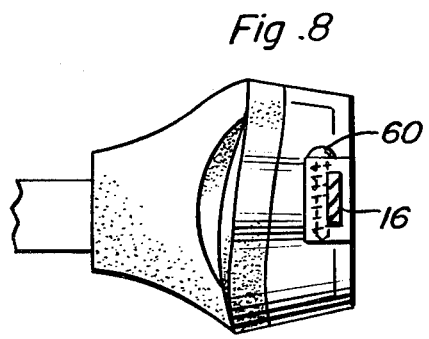
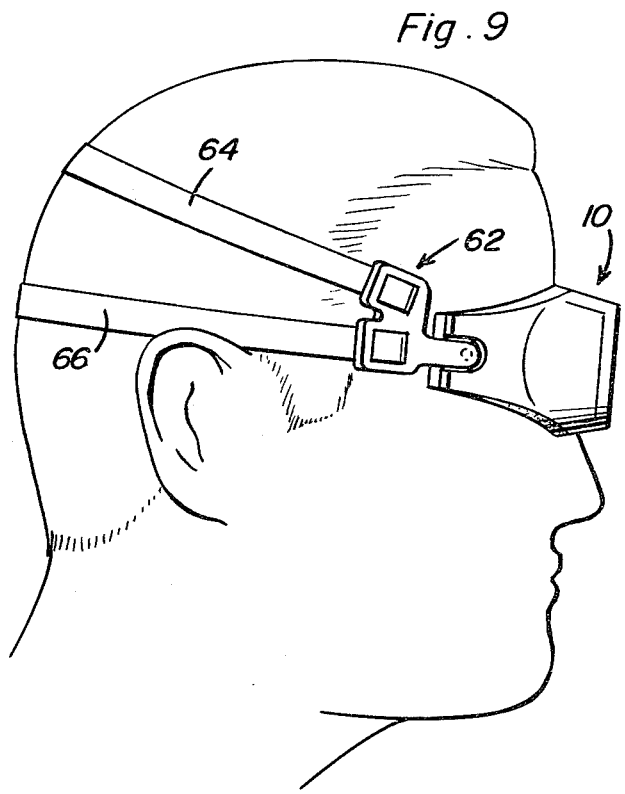
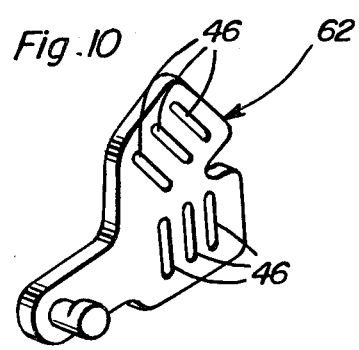

4,264,987

GOGGLES

CROSS-REFERENCE TO RELATED APPLICATION

This application is a continuation-in-part of U.S. application Ser. No. 957,009, filed Nov. 2, 1978 now abandoned.

BACKGROUND OF THE INVENTION

1. Field of the Invention

This invention relates to eye protectors and particularly to eye goggles which may be worn during swimming, skiing and other sports.

2. Description of the Prior Art

Many types of goggles for the protection of one's eyes during pursuit of athletic endeavors have been proposed in the past. Goggles used for athletic activities, especially those used when swimming, should be light in weight, easily attached and removed from the users' head, comfortable to wear, and streamlined. Also, when used for swimming the goggles must provide an adequate seal between the eye sockets of the user and the peripheral edge of the goggles in order that no water will enter the area interiorly of the goggles. Such water of course distorts vision and thereby hinders rather than aids the swimmer. Goggles proposed for the purpose of providing for the above-described needs include those shown in U.S. Pat. No. 4,051,557 issued Oct. 4, 1977 to Bengtson et al. The Bengtson et al goggles have a pair of identical eyepieces with each eyepiece having an upper and a lower incurved surface attached to padding for providing a water-tight seal between the goggles and the user. The Bengtson et al goggles also include a nosepiece formed with a plurality of stops for adjusting the nosepiece. This adjustment system is cumbersome and difficult to use. Also, the straps employed in the goggles do not allow an easy attachment of the goggles to the head of the user.

U.S. Pat. No. 2,264,351 issued Dec. 2, 1941 to Willson shows a headband strap for use with safety goggles. The goggles shown in the patent have eyepieces incorporating a curved surface to conform to the head of the user. Each eyepiece has a lateral excurved surface for making contact with the temple of the user and an incurved surface for contact with the skull surrounding the eye socket. The strap used in Willson includes an inelastic tubular head-band which provides a positive limit of stretch to a resilient member disposed in the head-band.

SUMMARY OF THE INVENTION

An object of the present invention is to provide a durable, comfortable and economical pair of goggles for use in swimming, skiing and other recreational sports.

Another object of the present invention is to provide a pair of goggles having eyepieces which conform more exactly to the shape of the bone structure surrounding the human eye socket so as to allow a water-tight seal to exist without the necessity of providing undue pressure on a foam pad and forcing the foam pad to conform to the required shape.

One more object of the present invention is to provide a pair of goggles the eyepieces of which extend into the eye socket and provides a slightly radially outward pressure to insure the watertight seal.

A further object of the present invention is to provide a pair of goggles having separate eyepieces which are connected by a unique and easily adjustable nosepiece for varying the distance between the eyepieces.

A still further object of the present invention is to provide a pair of goggles having a head strap which may be engaged and disengaged easily by the use of a hook and eye interconnection.

Yet a still further object of the present invention is to provide a head strap which may be adjusted easily to fit various sized heads.

An additional object of the present invention is to provide a pair of goggles which are configured to provide a minimum amount of water resistance when used by a swimmer.

Still another object of the present invention is to provide an embodiment of the invention including a double head strap configuration for insuring a positive connection between the straps and the head of the user.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 5 is a side view of the goggles showing the hook and eye interconnection.

FIG. 6 is a sectional view taken substantially along a plane passing through section line 6—6 of FIG. 5 and showing the hook and eye connection together with the adjustment mechanism for the strap.

FIG. 7 is a sectional view taken substantially along a plane passing through section line 7—7 of FIG. 1.

FIG. 8 is a sectional view taken substantially along a plane passing through section line 8—8 of FIG. 1.

FIG. 9 is an elevational view showing the goggles in use with the double head strap.

FIG. 10 is a perspective view of the hook portion used with the double head strap.

DESCRIPTION OF THE PREFERRED EMBODIMENT

Figure 1:
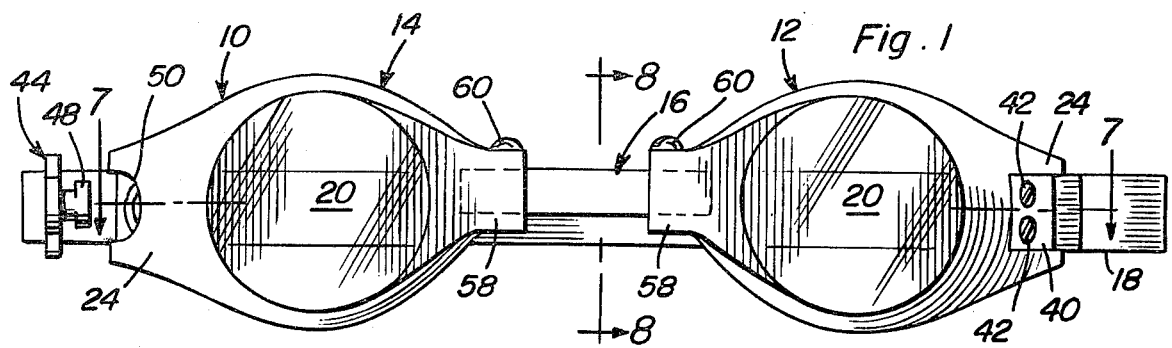
FIG. 1 is an elevational view of the goggles of the present invention.
Figure 3:
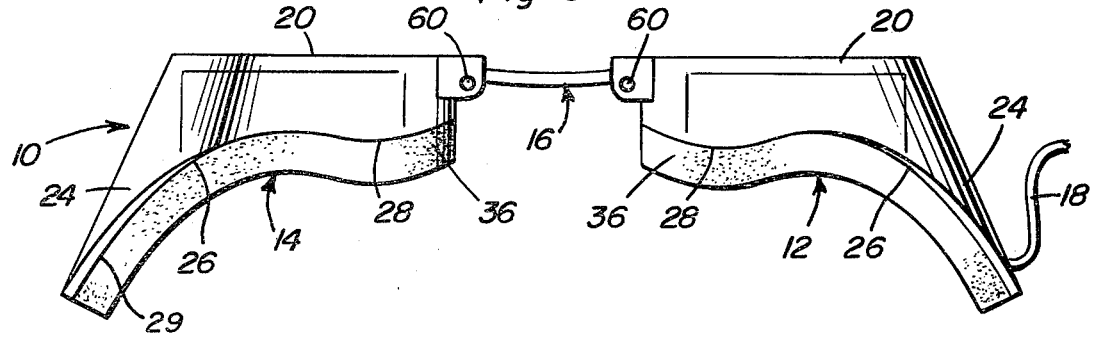
FIG. 3 is the bottom view of the goggles of the invention.

Now in reference to the drawings, goggles incorporating the principles and concepts of the present invention and generally designated by the numeral 10 will be clearly described. With particular reference to FIGS. 1 and 3, it will be noted that the goggles comprise two eyepieces 12 and 14 interconnected by nosepiece 16. A head band 18 is fixedly attached to eyepiece 12 and is removably attachable to eyepiece 14 for securing the goggles to the head of the user.

Figure 2:
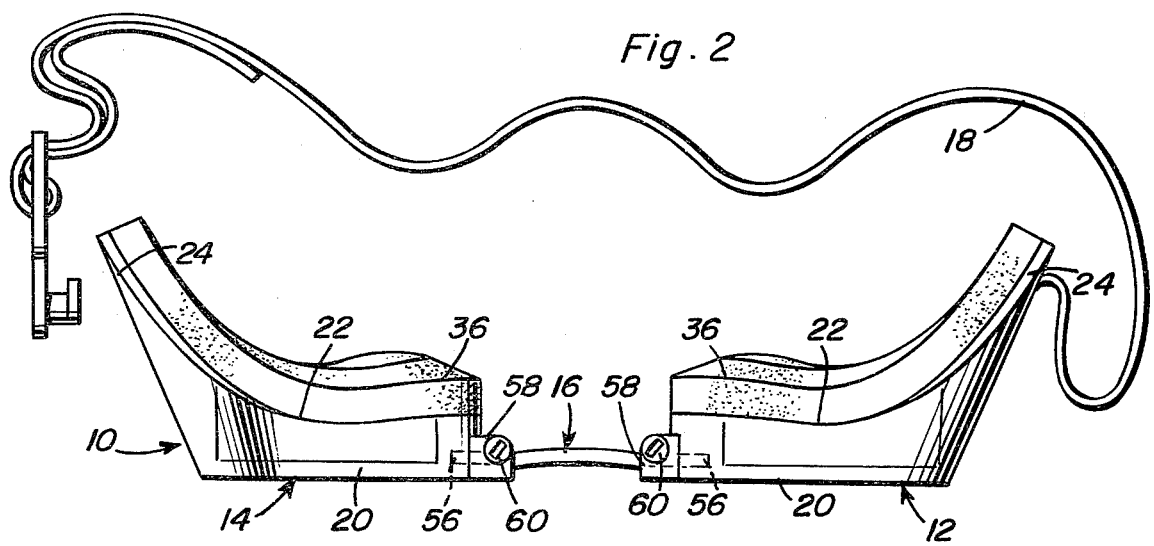
FIG. 2 is a plan view of the goggles of the present invention.
Figure 13:
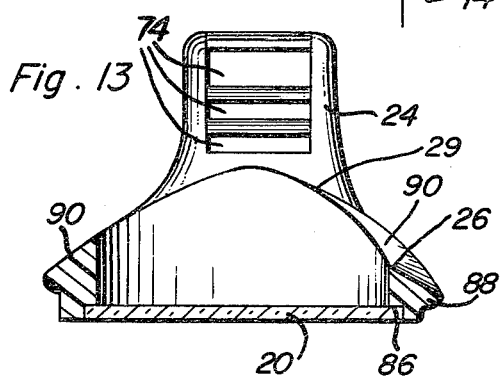
FIG. 13 is a sectional view taken substantially along a plane passing through section line 13—13 of FIG. 12.
Figure 15:
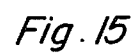
FIG. 15 is a perspective view of one eyepiece.
Figure 14:
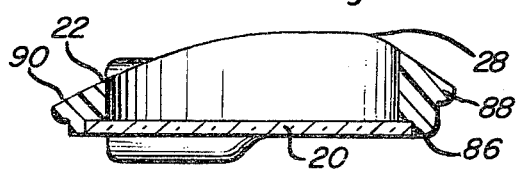
FIG. 14 is a sectional view taken substantially along a plane passing through section line 14—14 of FIG. 12.

Each eyepiece 12 and 14 is produced from clear optical plastic by, preferably, injection molding. Each eyepiece also includes a substantially planar lens portion 20 which may be either molded with the eyepiece from clear optical plastic or may be a pre-ground plastic lens adapted to fit into the pre-formed eyepiece. With reference to FIG. 2, it will be seen that the top contour of each eyepiece includes a transverse incurved portion 22 which is shaped to fit the upper portion of the human skull surrounding the eye socket. The transverse curve extends laterally and defines a wing section 24 which is designed to fit snugly against temporal area of the human skull. With reference to FIG. 3, it will be seen that the lower contour of each eyepiece includes a transverse incurved portion 26 beginning at the wings 24 and smoothly changing to a transverse excurved inside portion 28 which is designed to fit on the lower eye socket in the vicinity of the nose and a transverse excurved outside portion 29, see also FIGS. 13 and 14, is provided to conform to the facial bone contour defining the outer side marginal portion of the eye socket and all adjacent excurved and incurved portions merge smoothly into each other. This is to be contrasted with the bottom contour of the prior art shown in FIG. 4. In the prior art goggles, the curves 30 are incurved throughout their length and thereby leave a small gap in the area designated 32 when placed on the human head. This gap will have to be filled by proper compression of the foam rubber 34. In contrast, goggles of the present invention incorporate the use of foam pad 36 to merely effect a watertight seal between the plastic portion of the eyepiece and the skin of the user, the aforementioned gap existing in the prior art being filled by excurve portion 28 as discussed above.

As seen in FIG. 1, eyepiece 12 has attached thereto the head band 18. As seen in FIGS. 1 and 7, this attachment is effected through the use of an identation 38 made in the surface of the wing portion 24 of that eyepiece. The elastic head band 18 is inserted in the indentation and a cover plate 40 is fixedly attached thereover by the use of screw attachment devices 42 or any other suitable attachment means. On the opposite end of the head band 18 is attached hook portion 44. Hook portion 44 includes the adjustment mechanism of the device. As seen in FIG. 6, the adjustment portion comprises three laterally aligned transverse slots 46 through which the head band is woven in order to hold it in place. On the other end of the hook portion is the actual hook 48 which may be inserted in aperture 50 provided in eyepiece 14 for that purpose. Tension on the head band will maintain the flange 52 of the hook 48 in an engaged position within the aperture 50 in FIG. 6. The aperture 50 is an extension of an indentation 54 as seen in FIGS. 5 and 6. The indentation 54 is substantially equal in depth to the thickness of the hook portion 44 thus allowing a substantially flush arrangement between the hook portion and eyepiece when engaged.

As seen in FIGS. 1, 2, 3, 7 and 8, the nosepiece 16 fits within sockets 56 in each eyepiece. Each eyepiece also includes lateral extensions 58 through which sockets 56 also pass. Each lateral extension 58 has a screw 60 passing therethrough with the threads of the screw being in communication with its respective socket. In this manner, by inserting the elastic nosepiece 16 into the socket 56, the screw 60 must be turned in order to control the progress of the nosepiece 16 into the socket. The pressure of the screw against the nosepiece also serves to hold the nosepiece within the socket. Therefore, adjustment of the nosepiece 16 length may be effected through turning of the individual screws 60.

FIGS. 9 and 10 show a second embodiment of the hook portion of the invention. This embodiment is generally referred to by the numeral 62. Hook portion 62 is designed for use with two head bands 64 and 66. This configuration insures maximum positive support of the goggles on the head of the user. The hook portion 62 includes two series of laterally aligned slots 46. Each series of slots is for use with an individual one of the head straps. In this manner each head strap is individually adjustable by the user.

FIGS. 11–15 depict a pair of goggles 68 which are similar in many respects to goggles 10, with similar characteristics being represented by like numerals. Goggles 68 are compoed of a pair of eyepieces 70, 72 which are interconnected by a nosepiece 16. The eyepieces are held against the head of the user by a strap 18 and hook 14 which are those shown in FIG. 5. The hook is connected with an aperture formed in eyepiece 72. The opposite end of strap 16 is interwoven between three laterally aligned slots 74 formed in wing section 24 of the eyepiece 70. This provides for added adjustability and allows the eyepiece to be formed as a unitary construction.

The nosepiece 16 is held within a pair of opposed sockets 76 formed in the eyepieces 70, 72. Each socket has a threaded hole 78 disposed in one wall. A set screw 80 is screwed into each hole and is rotatably connected to a plate 82 which is mounted in the socket 76 for movement thereacross. Each plate 82 contains an opening through which a reduced extension 84 of the set screw passes. Obviously, with strap 16 inserted to the desired depth in sockets 78 between plates 82 and the opposite socket walls, set screws 80 can be tightened and the nosepiece adjustment will be completed.

Each eyepiece, as shown in relation to eyepiece 20, incorporates the transverse upper incurve 22 as well as the lower transverse incurved portion 26 and transverse excurved portion 28 in the vicinity of the nosepiece. These portions, as explained supra, are for the purpose of conforming to the external skull shape about the periphery of the eye socket. The transverse curves extend laterally to define a wing section 24 which, as discussed hereinabove, contains the strap attachments. The section of the eyepiece rimming the lens 20 is of a substantial thickness to provide rigidity and contains an annular reduced area 86 into which the lens is received thus making it flush with the front of the eyepiece. The lens can be mounted by gluing or in any other suitable manner.

Figure 11:
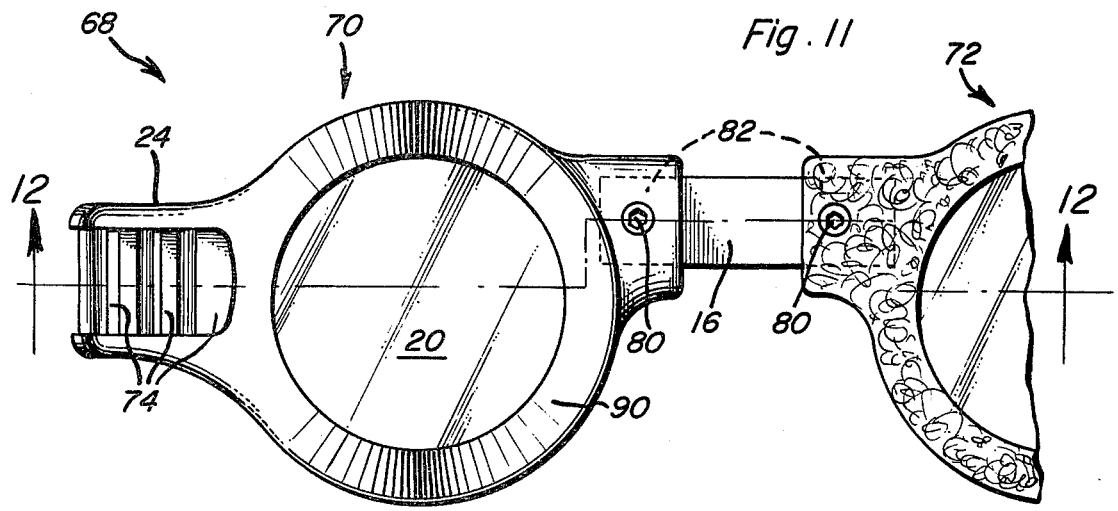
FIG. 11 is an elevational view of the goggles of the present invention showing one of the eye socket contacting surfaces.
Figure 12:
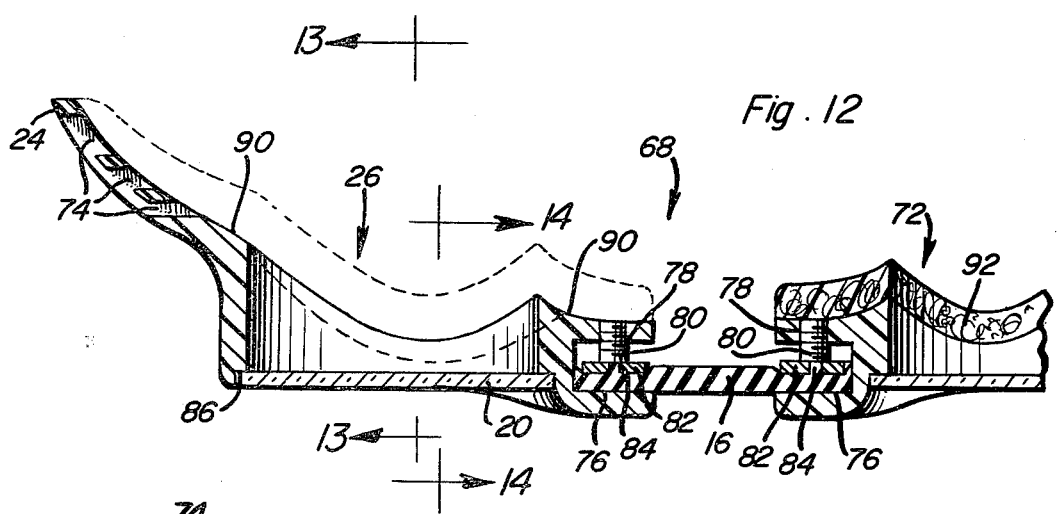
FIG. 12 is a sectional view taken substantially along a plane passing through section line 12—12 of FIG. 11.

Rearwardly of the lens, the eyepiece contains a radially outward flared portion 88 which results in a widened eye socket contacting surface 90. Surface 90 appears substantially annular in elevation, as seen in FIG. 11. However, when viewed in cross section, it becomes apparent that surface 90 is designed to promote an effective contact between the eyepiece and the skull of the user. In the area of wing 24, surface 90 slopes radially outward and away from the lens portion of the eyepiece and toward the temporal portion of the skull, when in use. The remainder of the surface slopes radially outward and forward, toward the front of the eyepiece so as to rest against the inside ridge of the eye socket with the inner edge of the surface 90 projecting slightly into the wearer's eye socket, and the outer edge projecting slightly outside of the eye socket. The surface 90 therefore abuts the outer edge of the eye socket and force is applied, through strap 18, both directly inward against the skull and radially outward against the rim of the eye socket. Since the surface 90 follows the incurves and excurves of the perimeter, the result is a convoluted surface which readily conforms to the eye socket. Accordingly, only a thin layer of foam padding, or the like, shown on eyepiece 72 at 92, need be employed to insure a watertight seal and maximum comfort to the wearer.

Figure 4:
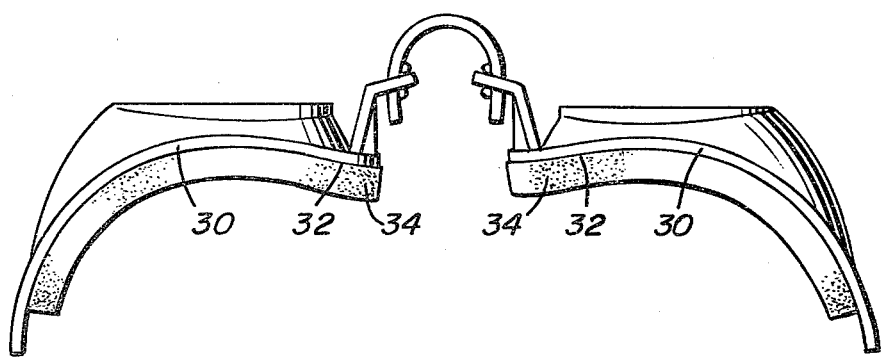
FIG. 4 is a bottom view of the prior art goggles.

This configuration is to be contrasted with that of the prior art, as shown in FIG. 4, wherein the skull contacting surfaces of the goggles are not sloped. The prior art goggles rely on the resiliency of the foam padding overlying the inner surfaces of the eyepieces to allow that padding to become contorted in a manner which will enable a watertight seal between the goggles and the skull of the user. A seal formed in this manner may be prone to leakage as well as the formation of pressure points which make the goggles uncomfortable to wear. The goggles of the present invention overcome these deficiencies.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. Goggles for use in athletic events and adapted to make a watertight seal around the eye of the wearer comprising: a pair of eyepieces interconnected by a flexible, elastic nosepiece, each eyepiece comprising an integrally formed body, said body having a lens portion and a head-fitting contour, said contour including a generally incurved upper portion for conforming to the upper eye socket of the user and a lower contour having an excurved portion for conforming to the eye socket of the user in the vicinity of the nose and an incurved portion for conforming to the eye socket in the area of the user's cheek bones, an eye socket contacting surface defined along said incurved upper portion and said lower contour, said surface sloping radially outward and toward the front of said goggles for producing a radial outward pressure on the eye socket of the user, and a head band fixedly attached to one eyepiece and removably attachable to the other eyepiece, said head band comprising two longitudinally extending elastomeric strips wherein one end of each strip is fixedly connected to one of said eyepieces and the opposite end of each strip is connected to an engaging means for removably engaging the other of said eyepieces.

2. The device of claim 1 wherein said removable engagement means comprises a hook portion for engagement with an aperture disposed in said other eyepiece, said hook portion having separate adjustment means thereon for engagement with each of said strips.

3. The device of claim 2 wherein each of said adjustment means comprises three longitudinally extending, laterally aligned slots.

4. The device defined in claim 1 wherein said adjustment means comprises a plate disposed in said socket and means for moving said plate across said socket for holding said elastomeric strip between said plate and one wall of said socket.

5. Goggles for use in athletic events and adapted to make a watertight seal around the eyes of the wearer comprising: a pair of eyepieces interconnected by a flexible, elastic nosepiece, each eyepiece comprising an integrally formed body, said body having a forward lens portion and a head-fitting portion contour, said contour including transverse generally incurved upper and lower portions for conforming to the forwardly facing surfaces of the human skull defining the upper and lower eye socket margins of the user and upstanding inside and outside excurved portions for conforming to the forwardly facing skull surfaces defining the inside and outside margins of the eye socket of the user in the vicinities of the nose and temporal areas of the skull, an eye socket contacting surface defined along said incurved and excurved portions, said surface sloping radially forward and outward toward the front of said goggles in the areas of said upper, inner and lower portions of said contour for producing a radially outward pressure on the eye socket of the user and sloping radially rearwardly and outwardly toward the rear of the goggles in the area of the outer portion of said contour, and a head band attached to and extending between the outer sides of the eyepieces for producing radial inward pressure on the temporal eye socket area of the user, the adjacent ends of said excurved and incurved portions as well as adjacent portions of said forwardly and rearwardly sloping surfaces merging smoothly together independent of abrupt changes in slope and radius of curvature.

6. The device of claim 5 wherein said eye socket contacting surface of each eyepiece is covered with a soft layer of foam cushion for effecting a seal between the eyepiece and the head of the user.

7. The device of claim 5 wherein said nosepiece comprises an elastomeric strip having two ends, each end being inserted in a socket disposed in a separate one of said eyepieces and being held therein by a rotatable adjustment means for gripping said elastomeric strip.

8. The device of claim 7 wherein said adjustment means comprises longitudinally extended rotatable element disposed transversely of said socket and having a portion in communication with said socket, said elastomeric strip being insertable between said rotatable element and one wall of said socket and being held therebetween by a frictional engagement.

9. The device of claim 5 wherein said head band has connected to one end thereof a hook portion for engagement with an aperture disposed in one of said eyepieces for providing said removable attachment.

10. The device of claim 9 wherein said hook portion includes a head band adjustment means for varying the length of said head band.

11. The device of claim 10 wherein said head band adjustment means comprises three longitudinally extending parallel slots disposed through said hook portion, said slots being laterally aligned with each other to allow an interweaving of said head band through said slots.

* * * * *